(12) United States Patent
Miura

(10) Patent No.: US 6,455,733 B1
(45) Date of Patent: Sep. 24, 2002

(54) APPARATUS AND METHOD FOR RECOVERING SORBIC ACID

(75) Inventor: Hiroshi Miura, deceased, late of Arai (JP), by Takashi Miura, legal representative

(73) Assignee: Daicel Chemical Industries, Ltd., Osaka (JP)

(*) Notice: Subject to any disclaimer, the term of this patent is extended or adjusted under 35 U.S.C. 154(b) by 0 days.

(21) Appl. No.: 09/341,576

(22) PCT Filed: Nov. 10, 1998

(86) PCT No.: PCT/JP98/05038

§ 371 (c)(1),
(2), (4) Date: Jan. 18, 2000

(87) PCT Pub. No.: WO99/25676

PCT Pub. Date: May 27, 1999

(30) Foreign Application Priority Data

Nov. 14, 1997 (JP) .......................... 09-313288
Apr. 27, 1998 (JP) .......................... 10-117490

(51) Int. Cl.$^7$ ............................. C07C 57/10
(52) U.S. Cl. ............................................. 562/601
(58) Field of Search ........................... 562/601

(56) References Cited

U.S. PATENT DOCUMENTS 3,758,563 A * 9/1973 Uematsu et al. ............ 260/526
3,992,442 A * 11/1976 Kageyama et al. ......... 260/526
4,371,505 A * 2/1983 Pautrot ........................ 423/10
4,639,294 A * 1/1987 Kamei et al. ................. 203/88

FOREIGN PATENT DOCUMENTS

JP          60152439          8/1985

* cited by examiner

Primary Examiner—Richard L. Raymond
Assistant Examiner—Zachary Tucker
(74) Attorney, Agent, or Firm—Birch, Stewart, Kolasch & Birch, LLP

(57) ABSTRACT

Crude sorbic acid produced in a decomposition step 1 is subjected to a crystallization step 2 to precipitate crystalline sorbic acid, and the crystalline sorbic acid is separated from a mother liquor (filtrate). The mother liquor was subjected to an extraction step 3 in which a specific extractant is employed, and an extract (organic phase) is subjected to a back extraction step 4 and treated with an alkaline solution to extract the sorbic acid into an aqueous phase in the form of a salt. The aqueous phase is neutralized in a neutralization step 6 and the produced sorbic acid is recovered in a separation step 7. As the extractant, use can be made of an organic solvent which is separable from water and has a solubility in water of not more than 1% by weight and in which not less than 0.5% by weight of sorbic acid is dissolvable (e.g., aliphatic $C_{6-20}$ alcohols, ketones, esters, aromatic ethers). According to the above process, sorbic acid can be recovered from a filtrate (mother liquor) produced in a sorbic acid production process with high recovering efficiency and therefore results in a consequent and effective reduction in the BOD of the waste liquid.

3 Claims, 1 Drawing Sheet

US 6,455,733 B1

APPARATUS AND METHOD FOR RECOVERING SORBIC ACID

This application is the national phase under 35 U.S.C. §371 of PCT International Application No. PCT/JP98/05038 which has an International filing date of Nov. 10, 1998 which designated the United States of America.

TECHNICAL FIELD

The present invention relates to an apparatus and a process for recovering sorbic acid with effectiveness.

BACKGROUND TECHNOLOGY

Sorbic acid is produced by decomposing (e.g., a decomposition using acids or alkalis, or thermal decomposition) a polyester prepared by reacting crotonaldehyde with ketene. Among such decomposition methods, acidolysis, particularly hydrolysis with hydrochloric acid is advantageous in view of yield and quality.

The production of sorbic acid utilizing a decomposition using hydrochloric acid is typically carried out by a recrystallization method comprising the steps of; reacting crotonaldehyde with ketene to prepare a polyester, heat-decomposing the polyester dispersed in hydrochloric acid, cooling and filtrating the reaction product to obtain a crude sorbic acid, dissolving the crude sorbic acid in hot water, hot-filtrating, and cooling the filtrate for crystallization, thereby producing purified sorbic acid. Since the recrystallization method involves the production of a large amount of a recrystallization mother liquor (filtrate) containing sorbic acid at a low concentration, efficient recovery of the sorbic acid from the mother liquor is difficult. Furthermore, the recrystallization mother liquor can not be discharged directly in view of environmental pollution because of the biochemical oxygen demand (BOD) of the mother liquor being high.

Japanese Patent Publication No. 13456/1986 (JP-B-61-13456) proposes a process for producing purified sorbic acid which comprises subjecting wet cakes of a crude sorbic acid prepared by acidolysis of a polyester to recrystallization, in which the pH of a dilute solution of the sorbic acid (recrystallization mother liquor) from the recrystallization step is adjusted to 5–7 and the resultant solution is concentrated by reverse osmosis, and from the resultant concentrated solution are recovered the precipitated crystals of sorbic acid. The literature mentions that the solvent extraction method is disadvantageous.

The method of the literature, however, requires an apparatus for the reverse osmosis, and a highly efficient recovery of sorbic acid with a simple apparatus and a simple operation with a consequent reduction in the BOD of the waste liquid (filtrate) cannot be expected. A technology for an effective and efficient reduction in the BOD has not been proposed yet.

Therefore, an object of the present invention is to provide an apparatus and a process for recovering sorbic acid that ensure a highly efficient recovery of sorbic acid from a waste liquid (e.g., crystallization mother liquor such as a filtrate) produced in a sorbic acid production step, such as in a recrystallization step.

Another object of the present invention is to provide an apparatus and a process for recovering sorbic acid that ensure an effective reduction in the BOD of a waste liquid and a recovery of highly pure sorbic acid from crude sorbic acid with high efficiency.

Another object of the present invention is to provide an apparatus and a process for recovering sorbic acid that enable an efficient recovery of highly pure sorbic acid from a waste liquid produced in the production of sorbic acid and also effectively reduce the BOD of the waste liquid by recycling an extracting solvent without a complicated apparatus and operation.

DISCLOSURE OF INVENTION

The inventor of the present invention did extensive investigations to attain the above objects, and found that sorbic acid can be extracted from a crystallization mother liquor with a high extractability by using a specific solvent, thereby the BOD of a waste liquid is significantly reduced. The present invention has been accomplished based on the above findings.

Accordingly, the recovering apparatus of the present invention is an apparatus for recovering sorbic acid from a waste liquid produced in a production step of sobic acid (e.g., in a recrystallization step of crude sorbic acid) by at least solvent extraction, which comprises an extraction unit for extraction of sorbic acid from the waste liquid using an organic solvent in which not less than 0.5% by weight of sorbic acid is dissolvable, separable from water, and having a solubility in water not more than 1% by weight. In this apparatus, for example, the crystalline sorbic acid formed by crystallization of crude sorbic acid may be separated from a waste liquid (a mother liquor) and the waste liquid may be subjected to the above-mentioned solvent extraction. The extract from the aforementioned solvent extraction unit may be treated with an alkali in a back (reverse) extraction unit to extract sorbic acid in the form of a salt. Moreover, the extract from the back extraction unit may be at least neutralized with an acid in a treatment unit followed by the separation of sorbic acid from the treated mixture in a separation unit. Furthermore, the organic solvent separated in the back extraction unit may be recycled to the extraction unit through a recycle line. As the extraction solvent, there may be used alcohols, ketones, hydrocarbons, esters, ethers, etc.

According to the process of the present invention, sorbic acid is recovered by extracting sorbic acid from the waste liquid (e.g., mother liquor) using the above organic solvent.

BEST MODE FOR CARRYING OUT THE INVENTION

Figure 1:
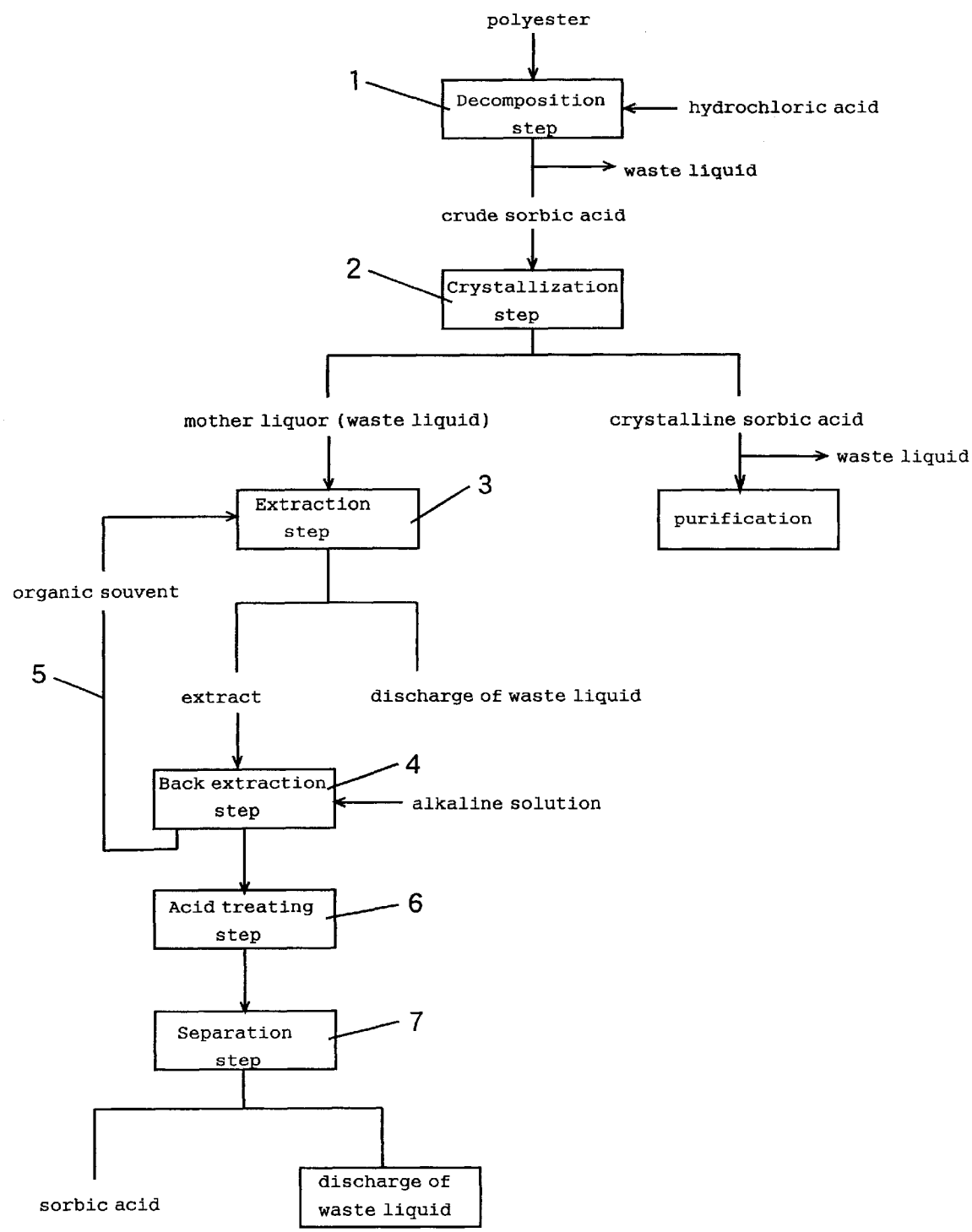
FIG. 1 is a flow chart showing an embodiment of a recovering process of the present invention.

Hereinafter, the present invention will be described in further detail with reference to the attached drawing where necessary.

The present invention is applicable to processes for recovering sorbic acid from a waste liquid produced in a production step of sorbic acid, e.g., to a process in which sorbic acid is recovered from a mother liquor (filtrate) produced by the recrystallization of crude sorbic acid. The production method of crude sorbic acid is not particularly restricted and includes various methods. To give an example, crude sorbic acid can be produced by (a) decomposition of a polyester formed by reacting crotonaldehyde with ketene, or by (2) condensation of crotonaldehyde with malonic acid. The polyester may be decomposed either with an acid or alkali, or by heat, and the production of crude sorbic acid by acidolysis of the polyester (particularly with inorganic acids, among others, hydrochloric acid) is industrially advantageous.

FIG. 1 is a flow chart showing an embodiment of the recovering process of the present invention.

For the separation of crystallized sorbic acid from a mother liquor (filtrate), the process of the embodiment comprises: a decomposition step (1) for decomposing a polyester formed by the reaction of crotonaldehyde with ketene with an acid (in this case, with hydrochloric acid) to form crude sorbic acid, and the crystallization step (2) for crystallizing or precipitating cristalline sorbic acid from the crude sorbic acid produced in the step (1). The product from the decomposition step (1) may be separated into the crude sorbic acid and a filtrate (waste liquid) by being subjected to a separation step such as filtration.

In the decomposition step (1), the decomposition of the polyester can be carried out by a conventional method, e.g., by mixing the polyester and an acid (particularly, hydrochloric acid) in an amount of about 2 to 7 times moles relative to the basic constitutive unit of the polyester with stirring at a temperature of 50 to 90° C. In the decomposition step, the decomposed polyester may be aged for isomerization, and the aging temperature can be selected from within the above-mentioned range.

In the decomposition step, sorbic acid is precipitated in the reaction system and, as described above, the reaction product is usually subjected to the separation step or process (e.g., filtration) to be separated into crude sorbic acid and a filtrate (waste liquid). The cakes of crude sorbic acid (wet cakes) are then subjected to the crystallization (or recrystallization) step (2).

In the crystallization step (2), from the crude sorbic acid is crystallized out purified sorbic acid and there is obtained crystalline pure sorbic acid. The crystallization of sorbic acid can be effected by dissolving the wet cakes of crude sorbic acid in hot water, mixing the mixture with heating together with active carbon, hot-filtrating the mixture, and cooling the resultant filtrate. Further, an organic or inorganic base (e.g., alkaline metal hydroxides such as sodium hydroxide) may be added to the mixture together with active carbon (activated carbon) as an adsorbent into convert the sorbic acid to its salt aiming at solubilization, and to the salt of sorbic acid may be added an acid (e.g., an inorganic acid such as hydrochloric acid) in the crystallization step to precipitate as a free sorbic acid. The crystalline sorbic acid undergone such crystallization is separated from a waste liquid (filtrate, mother liquor) by, e.g., filtration or centrifugation and then purified by a conventional purification procedure such as washing, recrystallization, and drying.

The waste liquid (mother liquor) separated off in such a manner is usually acidic (pH=about 2 to 4) and a dilute solution still containing sorbic acid at a concentration of about 0.01 to 0.3% by weight. Since the BOD of such waste liquid is usually about 4,000 to 200,000 ppm (moreover, the BOD of the waste liquid separated off during the decomposition step is, e.g., about 20,000 to 150,000 ppm), the discharge of the waste liquid contributes to the environmental pollution.

Therefore, for an efficient recovery of sorbic acid from the waste liquid and a consequent reduction in the BOD, according to the present invention, sorbic acid is extracted from the waste liquid with a specific extracting solvent (extactant) in an extraction step 3 (or an extraction unit).

The extraction solvent need only be poor in solubility in water but high in sorbic acid and separable from water, and can suitably be selected from hydrocarbons (e.g., aliphatic hydrocarbons, alicyclic hydrocarbons, aromatic hydrocarbons), halogenated hydrocarbons, alcohols, esters, ketones, ethers, and the like.

Particularly, preferred as the extracting solvent are those having a solubility in water, at a temperature of 20° C., of not more than 1% by weight (preferably not more than 0.5% by weight, more preferably not more than 0.3% by weight) and in which not less than 0.5% by weight of sorbic acid is dissolvable (preferably, not less than 1% by weight, more preferably not less than 3% by weight, and particularly not less than 5% by weight). Usually, these extracting solvents and water are different in specific gravity and the difference is 0.1 or more (e.g., about 0.1 to 0.3).

Such organic solvents include alcohols, hydrocarbons, esters, ketones, and ethers. These extracting solvents can be used either singly or as a combination of two or more species.

The alcohols include straight- or branched-chain alcohols having 6 or more carbon atoms, for example, straight- or branched-chain aliphatic $C_{6-20}$ alcohols such as hexanol, 2-methylpentanol, 2-methylhexanol, heptanol, dimethylpentanol, octanol, 2-ethylhexanol, capryl alcohol, nonyl alcohol, decyl alcohol, isodecyl alcohol, lauryl alcohol, myristyl alcohol, octadecyl alcohol, and oleyl alcohol; cycloalkanols ($C_{6-10}$cycloalkaonols such as cyclooctanol); and alkylcyclohexanols (e.g., $C_{1-4}$alkyl -$C_{5-10}$cycloalkanols such as methylcyclohexanol, trimethylcyclohexanol).

The aromatic hydrocarbons include, e.g., toluene and xylene, and the ketones include, e.g., aliphatic ketones (e.g., dialkyl ketones having 6 or more carbon atoms) such as dibutyl ketone, diisobutyl ketone, dipentyl ketone, methylamyl ketone, and methylhexyl ketone; and alicyclic ketones such as methylcyclohexanone.

The esters include organic acid-$C_{4-16}$alkyl esters and organic acid cycloalkyl esters, for example, acetic acid-$C_{4-16}$alkyl esters (particularly, acetic acid-$C_{6-16}$alkyl esters such as butyl acetate, isobutyl acetate, amylacetate, isoamylacetate, hexylacetate, 2-ethylbutyl acetate, octyl acetate, and 2-ethylhexyl acetate; cycloalkyl acetates (particularly, acetic acid-$C_{4-8}$cycloalkyl esters) such as cyclohexyl acetate and 2-methylcyclohexyl acetate; and the corresponding propionates and benzoates (e.g., methyl benzoate, ethyl benzoate, and butyl benzoate). The ethers include aliphatic ethers such as isopropyl ether, butyl ether, isobutyl ether, amyl ether, methyl butyl ether, methyl isobutyl ether, and ethyl butyl ether; and aromatic ethers such as anisole and phenetole. The preferred extractants are alcohols having 6 or more carbon atoms, ketones, hydrocarbons (e.g., aromatic hydrocarbons), organic acid $C_{6-16}$alkyl esters, organic acid cycloalkyl esters, and ethers (e.g., aromatic ethers). Among others, the use of a straight- or branched-chain $C_{6-20}$alcohol (particularly, a $C_{8-16}$alcohol) or a ketone as the extracting solvent permits highly efficient extraction of sorbic acid even used in a small amount relative to the waste liquid (e.g., filtrate).

In the extraction step 3, the amount of the extracting solvent S can suitably be selected according to the concentration of sorbic acid in the mother liquor, and may usually be selected from the ranges of about 10 to 250 parts by weight (S/F=0.1 to 2.5), preferably about 20 to 200 parts by weight (S/F=0.2 to 2), and more preferably about 25 to 150 parts by weight (S/F=0.25 to 1.5), per 100 parts by weight of the above-mentioned waste liquid (e.g., filtrate) F. Moreover, the extraction may be repeated a desired times, and how many times it is to be repeated may be selected from the range of 1 to 10 times, and particularly about 1 to 5 times. The extraction can be conducted at an appropriate temperature, e.g., at a temperature in the range of about 10 to 80° C., preferably about 20 to 70° C., and particularly about 30 to 60° C. In the extraction, it is industrially advantageous to use the extracting solvent at room temperatures (e.g., about 10 to 30° C.).

With the use of the above-mentioned extracting solvent, the sorbic acid in the mother liquor can be extracted into the organic phase with high efficiency and consequently the BOD of the water phase is remarkably reduced to, for example, 1,500 ppm or less (preferably, 1,000 ppm or less). Thus, the aqueous phase treated and separated from the extract (organic phase) in the extraction step (or by the extraction unit) 3 can be discharged with pollution load not so high.

To extract the sorbic acid in the form of a salt, the extract containing sorbic acid (organic phase) is treated with an alkali (an alkali solution) in a back (reverse) extraction step (a back extraction unit) 4. Although an organic base such as an amine can be used as the alkali, inorganic bases are advantageous from the industrial standpoint. The inorganic bases include, besides ammonia, alakline metal hydroxides (e.g., lithium hydroxide, sodium hydroxide, potassium hydroxide); alkaline metal carbonates (e.g., sodium carbonate); and alkaline metal hydrogencarbonates (e.g., sodium hydrogencarbonate). Usually, the alkali can be used in the form of an aqueous solution, and its concentration is not particularly limited and usually about 3 to 15% by weight and preferably about 5 to 10t by weight (e.g., 5 to 8% by weight).

The amount of the alkali is selected according to the concentration of the sorbic acid or other acid component in the extract (organic phase), and usually selected from within the range of about 0.5 to 2 equivalents (e.g., 0.7 to 1.5 equivalents) of the alkali and particularly about 1 to 2 equivalents of the alkali per 1 mole of sorbic acid. When using an aqueous solution containing 7.5% by weight of sodium hydroxide, the ratio of the extract (organic phase) to the alkaline aqueous solution is the former/ the latter=about 0.1 to 20 (weight ratio), preferably about 0.2 to 10 (weight ratio), and more preferably about 0.5 to 5 (weight ratio).

For a greater separation efficiency of the organic phase and the aqueous phase, the sorbic acid concentration in the back extraction step is, e.g., about 3 to 25% by weight and preferably about 3 to 20% by weight (e.g., 3 to 15% by weight).

In the back extraction step (or the back extraction unit) 4, the extract from the step 3 is further separated into the extract (aqueous phase) to which the sorbic acid salt is transferred, and the organic solvent (organic phase). The separated organic solvent (organic phase) is sent back to the extraction step (or the extraction unit) 3 through the line 5 and reused for solvent extraction.

The extract containing the sorbic acid salt (aqueous phase) is at least neutralized with an acid in a treatment step 6 (or treatment unit) to generate or produce a free sorbic acid. As the acid, an organic acid separable from the sorbic acid by a conventional separation method such as distillation (e.g., acetic acid) can be used, and an inorganic acid (e.g., hydrochloric acid, nitric acid, sulfuric acid, particularly hydrochloric acid) is generally employed. The pH of the acid-treated solution is, for example, about 1 to 4 and preferably about 2 to 3. The acid treatment allows the sorbic acid to precipitate in the form of crystals. Thus, the acid-treated solution subjected then, to a separation step (or separation unit) 7, separation by filtration, centrifugation, etc., can be separated into highly pure crystalline sorbic acid and an aqueous phase containing a salt and the like. The sorbic acid can be recovered by purifying and drying the sorbic acid if necessary. The aqueous phase containing the salt and the like can be discharged with pollution load not high.

According to the above process, highly pure sorbic acid of 98% and higher purity can be recovered with a recovering efficiency of not less than 98%.

As for the extraction unit or the back extraction unit, there may be employed conventional ones, such as a tank extractor equipped with a stirring tank and a separatory tank (standing tank), a tower extractor (extraction columns) such as a packed tower or column (e.g., Raschig ring packed column), a perforated plate tower, a spray tower, and a pulsed extraction column (pulse column), and a jet extractor with violent agitation, and a rotary extraction unit such as a rotary extractor. In the extraction and back extraction, the extract and the extractant or the alkali can flow countercurrently. In the back extraction unit, the back extraction can be carried out with the alkali solution circulating, and if necessary, with the solution being supplied with the alkali in an amount equal to the consumed and the solution in an amount equal to the supplied alkali solution being drawn off the system.

Furthermore, the present invention can be applied to a process for recovering sorbic acid from a sorbic acid-containing waste liquid produced in the production process of the same, and the origin of the waste liquid is not particularly limited. To give an example, while in the above example sorbic acid is extracted from the waste liquid produced in the crystallization step, sorbic acid can be extracted either from the waste liquid produced in the decomposition step 1 or the waste liquid produced in the crystallization step 2. Preferably, the present invention is adopted at least for the recovery of sorbic acid from the waste liquid produced in the crystallization step.

In the present invention, each or some steps may be carried out in batches, or all steps in succession.

INDUSTRIAL APPLICABILITY

According to the present invention, there can be realized a highly efficient recovery of sorbic acid from a waste liquid produced in the production process of the same by using a specific organic solvent. Moreover, not only an effective reduction in the BOD of the waste liquid but also a highly efficient recovery of sorbic acid of high purity can be achieved. Further, highly pure sorbic acid can be recovered, with high recovering efficiency, from a waste liquid produced in the sorbic acid production process not with a complex device or operation but with such simple operations as extraction and back extraction, and the BOD of the waste liquid can effectively be reduced by recycling the extracting solvent.

EXAMPLES

The following examples are intended to describe this invention in further detail and should by no means be interpreted as defining the scope of the invention.

In the following examples and comparative examples, sorbic acid was recovered from a waste liquid (mother liquor) described below.

To 100 parts by weight of a polyester formed by reacting crotonaldehyde with ketene was added 380 parts by weight of concentrated hydrochloric acid, and the mixture was heated at 60° C. for 2 hours for hydrolysis. The reaction mixture was cooled to room temperature to precipitate the crystals of crude sorbic acid out. The crystals of crude sorbic acid (100 parts by weight), were mixed with 5 parts by weight of active carbon and 95 parts by weight of an aqueous solution containing 25% by weight of sodium hydroxide, and the mixture was heated. Then, the active carbon was hot-filtered, and sorbic acid was precipitated out by adjusting the pH of the filtrate to 2–3 by adding concentrated hydrochloric acid thereto. The crystallized sorbic acid was filtered off to give a filtrate (mother liquor).

Example 1

As the mother liquor, a filtrate containing 2,904 ppm of sorbic acid and 3,626 ppm of other component (e.g., organic acid) (total: 6,530 ppm) was used. The mother liquor F1 and an extracting solvent S1 are fed into a solvent extraction column (40 mmϕ×1,000 mm, packed with Raschig rings 5 mmϕ×5 mm) at a predetermined flow (L/H) and a predetermined ratio (S1/F1=2), and the charge was subjected to extraction treatment to be separated into an organic phase and an aqueous phase. The extractability was calculated by measuring the sorbic acid concentration in the water phase by high performance liquid chromatography. The results are shown in Table 1.

| Organic Solvent | Residual amount in the aqueous phase (ppm) | | | Extractability (%) | | |
|---|---|---|---|---|---|---|
| | Sorbic acid | Other component | Total | Sorbic acid | Other component | Total |
| (1) Mother liquor (filtrate) | 2904 | 3626 | 6530 | | | |
| n-hexane | 632 | 3147 | 3779 | 78.2 | 13.2 | 42.1 |
| n-decane | 679 | 3614 | 4293 | 76.6 | 0.3 | 34.3 |
| (2) Mother liquor (filtrate) | 2855 | 2395 | 5250 | | | |
| anisole | 29 | 1384 | 1423 | 99.0 | 42.2 | 72.9 |
| xylene | 119 | 1520 | 1639 | 95.8 | 36.5 | 68.8 |
| n-octyl alcohol | ND | 1560 | 1560 | 100 | 34.9 | 70.3 |
| n-decyl alcohol | ND | 1435 | 1435 | 100 | 40.1 | 72.7 |
| isodecyl alcohol | ND | 1429 | 1429 | 100 | 40.3 | 72.8 |
| diisobutyl ketone | 14 | 1710 | 1724 | 99.5 | 28.6 | 67.2 |
| toluene | 103 | 2328 | 2430 | 96.4 | 2.8 | 53.7 |
| 2-ethylhexanol | ND | 1204 | 1204 | 100 | 49.7 | 77.1 |
| 2,6-dimethyl-4-pentanol | 46 | 1017 | 1063 | 98.4 | 57.5 | 79.8 |
| cyclohexyl acetate | 15 | 1323 | 1338 | 99.5 | 44.8 | 74.5 |
| 2-ethyl butyl acetic acid | 7 | 852 | 859 | 99.8 | 64.4 | 83.6 |
| 2-methylcyclohexyl acetic acid | 4 | 794 | 798 | 99.9 | 66.8 | 84.8 |
| isoamyl propionate | 14 | 866 | 880 | 99.5 | 63.8 | 82.8 |
| ethyl benzoate | 13 | 1394 | 1407 | 99.5 | 41.5 | 73.2 |

380 parts by weight of concentrated hydrochloric acid was added to 100 parts by weight of a polyester produced by reacting crotonaldehyde with ketene, and the mixture was heated to 80° C. The mixture was aged at 75° C. for 60 minutes and cooled to 25° C. over one hour to precipitate the crystals of crude sorbic acid. The crystals of crude sorbic acid (100 parts by weight) were mixed with 5 parts by weight of active carbon and 95 parts by weight of a 25% sodium hydroxide aqueous solution. While heating the mixture, the active carbon was filtered off, and the pH of the filtrate was adjusted to 2–3 by adding concentrated hydrochloric acid thereto to precipitate sorbic acid out. The crystalline sorbic acid was filtered off to give a filtrate (mother liquor).

Using this mother liquor, the same extraction process was carried out as in Example 1. The results were the same as those in Example 1.

Example 2

As the mother liquor, a filtrate containing 2,320 ppm of sorbic acid and 5,373 ppm of other component (e.g., organic acid)(total: 7,694 ppm) was used. Except that the mother liquor F1 and an extracting solvent S1 were fed into the solvent extraction column at a flow ratio (S1/F1)=1 or (S1/F1)=0.5 as shown in Table 2, the charge was subjected to the extraction steps in the same manner as in Example 1. The sorbic acid concentration in the aqueous phase was measured by high performance liquid chromatography, and the extractability was calculated based thereon. The results are shown in Table 2.

TABLE 2

| | Organic solvent | Residual amount in the water phase (ppm) | | | Extractability (%) | | |
|---|---|---|---|---|---|---|---|
| | | Sorbic acid | Other component | Total | Sorbic acid | Other component | Total |
| S/F = 1 | (3) Mother liquor (filtrate) | 2320 | 5374 | 7694 | | | |
| | n-hexane | 971 | 5331 | 6502 | 58.1 | 0.8 | 18.1 |
| | anisole | 175 | 4501 | 4676 | 92.5 | 16.2 | 39.2 |
| | (4) Mother liquor (filtrate) | 2485 | 2648 | 5133 | | | |
| | xylene | 284 | 2467 | 2751 | 88.6 | 6.8 | 46.4 |
| | n-octyl alcohol | 10 | 1510 | 1520 | 99.6 | 43.0 | 70.4 |
| | isodecyl alcohol | 11 | 1449 | 1460 | 99.6 | 45.3 | 71.6 |
| | n-decylalcohol | 13 | 1503 | 1516 | 99.5 | 43.2 | 70.5 |
| | diisobutyl ketone | 23 | 1830 | 1853 | 99.1 | 30.9 | 63.9 |
| S/F = 0.5 | (3) Mother liquor (filtrate) | 2320 | 5374 | 7694 | | | |
| | n-hexane | 1213 | 5439 | 6652 | 47.7 | 0 | 13.5 |
| | anisole | 289 | 5201 | 5490 | 87.5 | 3.2 | 28.6 |
| | (4) Mother liquor (filtrate) | 2485 | 2648 | 5133 | | | |
| | xylene | 310 | 2011 | 2321 | 87.5 | 24.1 | 54.8 |
| | n-octyl alcohol | 72 | 1425 | 1497 | 97.1 | 46.2 | 70.8 |

TABLE 2-continued

| Organic solvent | Residual amount in the water phase (ppm) | | | Extractability (%) | | |
| --- | --- | --- | --- | --- | --- | --- |
| | Sorbic acid | Other component | Total | Sorbic acid | Other component | Total |
| isodecyl alcohol | 71 | 1519 | 1590 | 97.1 | 42.7 | 69.0 |
| diisobutyl ketone | 144 | 2019 | 2163 | 94.2 | 23.8 | 57.9 |

As obvious from Tables 1 and 2, the extraction with a specific extractant considerably reduces the sorbic acid content in the waste liquid (mother liquor) and the BOD thereof. The BOD is nearly equivalent to 1.5 times the sorbic acid content (unit: ppm).

Example 3

As the mother liquor, a filtrate containing 2,855 ppm of sorbic acid and 2,395 ppm of other component (e.g., organic acid)(total: 5,250 ppm) was employed. The mother liquor and n-octanol were fed into a solvent extraction column (40 mm$\phi$×1,000 mm, packed with Raschig rings 5 mm$\phi$×5 mm) at flows of 1L/H and 2L/H (flow ratio S/F=2), respectively, and the charge was subjected to the extraction steps to be separated into the organic phase and the aqueous phase. In the analysis by high performance liquid chromatography, no sorbic acid was detected in the aqueous phase (extractability: 100%), and 1,560 ppm of other component (extractability: 34.9%) was detected. The total extractability was 70.3%, indicating a great reduction in the BOD.

The above-mentioned sorbic acid-containing organic phase and an aqueous solution containing 7.5% by weight of sodium hydroxide were fed into a back extraction column (40 mm$\phi$×1,000 mm, packed with Raschig rings 5 mm$\phi$×5 mm) at flows of 2L/H and 1L/H (flow ratio: S/F=2), respectively, and the charge was separated into the organic phase and the aqueous phase with the sorbic acid extracted into the aqueous phase in the form of sodium sorbate. Analysis of the contents in the organic phase and the aqueous phase by high performance liquid chromatography revealed no sorbic acid in the organic phase, and 2,734 ppm of sorbic acid (extractability: 101%) and 816 ppm of other component in the aqueous phase, indicating highly efficient back extraction of sorbic acid.

The organic phase from the back extraction column was stored in a storage tank and reused as the extracting solvent. On the other hand, to 100 parts by weight of the aqueous phase was added 3 parts by weight of 35% hydrochloric acid to precipitate the sorbic acid contained in the aqueous phase out. The precipitated sorbic acid was filtered off and dried, and there is obtained sorbic acid having a purity of 98% or higher with a recovering efficiency of not less than 98%. The above steps were successively carried out.

We claim:

1. A process for recovering sorbic acid from a sorbic acid-containing waste liquid produced in a sorbic acid production process by at least solvent extraction, which comprises extracting sorbic acid from the waste liquid using an organic solvent which is separable from water and has a solubility in water of not more than 1 % by weight and in which not less than 0.5% by weight of sorbic acid is dissolvable, wherein the organic solvent is at least one member selected from the group consisting of alcohols having 6 or more carbon atoms, aliphatic or alicyclic $C_{6-11}$ ketones, organic acid $C_{6-16}$ alkyl esters, organic acid cycloalkyl esters, and aliphatic or aromatic $C_{5-10}$ ethers.

2. An apparatus for recovering sorbic acid by decomposing a polyester to produce a crude sorbic acid, crystallizing sorbic acid from the crude sorbic acid, and separating the crystalline sorbic acid from a waste liquid, which apparatus is provided with:

an extraction unit comprising an organic solvent which is separable from water and at least one member selected from the group consisting of alcohols having 6 or more carbon atoms, aliphatic or alicyclic $C_{6-11}$-ketones, organic acid $C_{6-16}$-alkyl esters, organic acid cycloalkyl esters, and aliphatic or aromatic $C_{5-10}$-ethers;

a back extraction unit comprising an alkali;

a line for recycling an organic solvent separated in the back extraction unit to the extraction unit;

a treatment unit comprising an acid; and a separation unit comprising a filter or a centrifuge.

3. The apparatus of claim 2, wherein said extraction unit comprises an organic solvent selected from the group consisting of $C_{6-20}$-alcohols and aliphatic or alicyclic $C_{6-11}$-ketones.

* * * * *